US006420425B1

(12) United States Patent
Melman

(10) Patent No.: US 6,420,425 B1
(45) Date of Patent: Jul. 16, 2002

(54) METHOD FOR THE BROAD BASED TREATMENT OF INFECTIONS ESPECIALLY INFECTIONS OF ORGANS SUCH AS THE SKIN AND VAGINA

(76) Inventor: Steven A. Melman, 8909 Iverleigh Ct., Potomac, MD (US) 20854

( * ) Notice: Subject to any disclaimer, the term of this patent is extended or adjusted under 35 U.S.C. 154(b) by 0 days.

(21) Appl. No.: 09/346,293

(22) Filed: Jul. 2, 1999

Related U.S. Application Data

(63) Continuation of application No. PCT/US98/04761, filed on Jan. 2, 1998, which is a continuation of application No. 08/778,269, filed on Jan. 2, 1997, now Pat. No. 5,853,767.

(51) Int. Cl.$^7$ .......................... A61K 31/19; A61K 33/22
(52) U.S. Cl. ........................ 514/557; 424/659; 514/967
(58) Field of Search .......................... 424/659; 514/967, 514/557

(56) References Cited

U.S. PATENT DOCUMENTS

| 5,158,774 A | 10/1992 | Inman ........................ 424/430 |
| 5,266,329 A | 11/1993 | Riley, Jr. ..................... 424/430 |
| 5,292,532 A | 3/1994 | Bombart ..................... 424/405 |
| 5,451,335 A | 9/1995 | Hieatt et al. .................. 252/82 |
| 5,480,658 A | 1/1996 | Melman ..................... 424/659 |
| 5,489,435 A | 2/1996 | Ratcliff ....................... 424/422 |
| 5,573,765 A | * 11/1996 | Reinhard et al. ......... 424/93.45 |

OTHER PUBLICATIONS

Asikoglu et al, The Release of Isoconazole Nitrate From Different Suppository Bases: In–vitro Dissolution, Physiochemical and Microbiological Studies, 1995.
Hart, "Boric Acid Vaginal Suppositories", The Annals of Pharmacotherapy, vol. 27, Nov. 1993, pp. 1355–1357.
Jain, S.K. et al, "Fungitoxic effect of some organic volatile substances against fungi causing otomycosis", Mycoses, vol. 37, 1994, pp. 299–301.
Redondo–Lopez, V. et al, "*Torulopsis glabrata* Vaginitis: Clinical Aspects and Susceptibility to Antifungal Agents", Am. J. Obstet. Gynecol., vol. 76, No. 4, Oct. 1990, pp. 651–655.
Swate, T.F. et al, "Boric Acid Treatment of Vulvovaginal Candidiasis", Am. J. Obstet. Gynecol., vol. 43, No. 6, Jun. 1974, pp. 893–895.
van Slyke, K.K. et al, "Treatment of vulvovaginal candidiasis with boric acid powder", Am. J. Obstet. Gynecol., vol. 141, No. 2, Sep. 15, 1981, pp. 145–148.

Erkan, M. et al, "Treatment of otomycosis with acetic and boric acid", Revista Iberoamericana de Micologia, vol. 10, 1993, pp. 33–35.
Rein, M.F., Nystatin vs. Boric Acid Powder in Vulvovaginal Candidiasis, Correspondence, vol. 144, No. 8, pp. 992–993.
Chapter 9 of Systemic Fungal Diseases, pp. 148–150, Merck Manual of Diagnosis and Therapy (15$^{th}$ Ed.), Merck & Co. Inc. 1989.
Sale of Veterinarial Ear Cleaner at Trade Show on Sep. 20, 1992. Formulation of cleanser sold is same as on batch record dated Nov. 18, 1992.
Biological Abstracts 96:100793 (1993).
Chapter 177, Common Gynecological Problems, Vaginal Discharge And Inflammation, pp. 1674–1676, Merck Manual of Diagnosis And Therapy (15$^{th}$ Ed.), Merck & Co. Inc., 1989.
Nyirjesy, P. et al, "Chronic fungal vaginitis: The value of Cultures", Am. J. Obstet. Gynecol., vol. 173, No. 3, 1995, pp. 820–823.
Package Insert: Floraquin Vaginal Tablets®, G.D. Searle Ltd., South Africa, Feb. 13, 1975.
Label from Oticlean®—A Ear Cleaning Lotion For Dogs and Cats manufactured by ARC Laboratories, 1980.
Label from R–7 Ear Cleaner, manufactured by Gimborn U.S.A. 1989.
Bausch & Lomb brand Acetic Acid 2% Aluminum Aceate (Borofair) manufactured by Pharmafair, Dec. 26, 1991.

* cited by examiner

Primary Examiner—Theodore J. Criares
Assistant Examiner—Jennifer Kim
(74) Attorney, Agent, or Firm—Corinne Pouliquen; Katten Muchin Zavis Rosenmam

(57) ABSTRACT

A method for treating and preventing infections, bacterial, fungal, insecticidal, parasitic and actinomycotic in origin, especially infections of organs such as the vagina and skin. The methods involves administering to a patient in need thereof a composition comprising a combination of boric acid and acetic acid, in effective amounts. Such a composition is especially useful as a broad based treatment and prevention of vaginal and skin infections of unknown origin and can be used without the need for medical diagnosis or while such a diagnosis is being determined. Such a composition is effective, safe, economical and environmentally friendly, and provides an alternative to existing forms of treatment which are toxic which may cause undesirable side effects.

14 Claims, No Drawings

METHOD FOR THE BROAD BASED TREATMENT OF INFECTIONS ESPECIALLY INFECTIONS OF ORGANS SUCH AS THE SKIN AND VAGINA

CROSS REFERENCE TO RELATED APPLICATIONS

This application is a continuation application of PCT/US98/04761, filed Jan. 2, 1998, which is a continuation U.S. application Ser. No. 08/778,269, filed Jan. 2, 1997, now U.S. Pat. No. 5,853,767.

FIELD OF INVENTION

This invention relates generally to a method for the treatment of infections, fungal, bacterial, parasitic, insecticidal and actinomycotic in origin, especially infections of organs such as the vagina and skin. This invention further relates to a composition in a form suitable for treating vaginal infections and skin conditions and in the prevention of such infections and conditions.

BACKGROUND OF THE INVENTION

Vaginitis is a frequent cause of distress and discomfort in adult women accounting for about 10 million physician office visits per year in the U.S. The three major causes of this inflammation and the corresponding symptoms of abnormal discharge, itching, burning, dyspareunia and dysuria, include vaginal candidiasis, bacterial vaginosis and trichomonas.

Traditionally the treatment for vaginal and ear candidiasis has been the imidazole/triazole related antifungal compounds. These compounds are primarily effective against *Candida albicans* and provide little to no relief from *Torulopsis glabrata* and *Candida tropicalis*. While terconazole is effective against non-albicans yeast as well as albicans, its use is limited to infections caused by the genus Candida, for example, vulvovaginitis. The recent introduction of over the counter imidazole/triazole compounds such as miconazole, clotrimizole and butconazole is therefore problematic. These compounds are limited in their application being only efficacious against particular types of infection, for example, infection caused by the genus Candida, as in vaginal candidiasis. Without proper testing it is not possible for a patient to know whether they suffer from, for example, vaginal candidiasis or bacterial vaginosis, the symptoms being similar. In other words, what the nature and origin of the infection is.

Additional active ingredients used in the treatment of vaginal candidiasis include sulfanilamide and nystatin. These compounds again are only effective against the genus Candida and prior to their use the diagnosis of vaginal candidiasis should be confirmed by laboratory analysis, such as, cytology including KOH smears, giemsa, Wrights and other stains and/or cultures and/or biopsy. Such diagnosis can mean that proper treatment is delayed. Common treatments for bacterial vaginosis include oral metronidazole and clindamycin vaginal cream or oral. Metronidazole taken orally causes gastrointestinal distress, creates a metallic taste for the course of treatment and has been shown to be carcinogenic in mice and rats. Clindamycin therapy has been associated with severe colitis which may end fatally. Additionally, while these compositions are effective in eliminating the bacterial vaginosis, their use, as with any antibiotic use, may cause yeast propagation and resulting vaginal candidiasis.

Trichomonas and related parasites are treated with antibiotics such as metronidazole.

There is currently no product available, either over the counter or by prescription, that may be used to safely and effectively treat, for example, vaginal infections of both bacterial and fungal origin. It would therefore be extremely advantageous to provide such a product that can be used for the treatment of vaginal infection such as symptomatic vaginal discharge, vaginitis and the like in which the cause, based on the symptoms alone, may be indeterminable without specific medical diagnosis. Furthermore it would be advantageous to provide a product which may be used as an interim treatment, or first choice treatment, while actual diagnosis is being determined and to provide an alternative to existing treatment products which may be toxic, expensive and environmentally unfriendly and which may also cause side effects, such as, in the case of antibiotics which can ironically cause vaginal candidiasis.

Acetic acid is known to have antimicrobial capacities and is effective at various percentages against Pseudomonas, Staphylococcus, Streptococcus and various yeasts. The fungitoxic effects of acetic acid on fungi causing otomycosis has been examined in *Mycoses* 37: 299–301 (1994). In this study various volatile compounds, including acetic acid, were tested, in vitro, for their fungitoxic effects against five fungi. Some antifungal effect was illustrated for acetic acid. *Candida albicans* was shown to be the most resistant to the volatiles. Boric acid is known to be an effective antibacterial and antifungal agent and has been prepared in the form of a suppository for the treatment of fungal infection alone (see *The Annals of Pharmacotherapy* 1993, Volume 27, pp.1355–1357). Boric acid has been shown to be fungistatic against *Candida albicans* in vitro and effective in treating vulvovaginal candidiasis (see *Obstet. Gynecol.*, (1974) 43:893–895, "Boric Acid Treatment of Vulvovaginitis").

Acetic acid and boric acid have been used separately in vivo for the treatment of otomycosis (see *Revista Iberoamericana de Micologia* (1993):10: pp. 33–35). In this study two groups of patients were tested. Group A patients were treated with a combination of acetic acid (2%), hydrocortisone (1%) and sterile water (to 100%). Group B patients were treated with boric acid (4%) saturated in absolute alcohol (25%) and sterile water (to 100%). A composition comprising both acetic acid and boric acid was not used.

A solution comprising, as active ingredients, both acetic acid and boric acid is disclosed in U.S. Pat. No. 5,480,658, the disclosure of which is expressly incorporated herein by reference. The composition as described in this patent is useful in cleaning the ears of pets.

A composition comprising acetic acid and boric acid, in particular amounts, has now surprisingly been found to be synergistically effective in the broad based treatment of bacterial, fungal, insecticidal, parasitic and actinomycotic infection and in the treatment of keratinization disorders, i.e., the composition has been found to have bacteriostatic, bacteriocidal, anti-fungal, fungicidal, fungistatic and keratolytic properties and is particularly useful in the treatment of skin and vaginal infections. The composition is also effective in the prevention of such infections and provides a safe, effective, economical and environmentally friendly alternative to existing forms of treatment and prevention of such infections.

SUMMARY OF INVENTION

In accordance with one embodiment of the present invention, a method for the broad based treatment of vaginal infection is provided comprising administering to a patient in need thereof an effective amount of a composition which comprises both acetic acid and boric acid, and a pharmaceutically acceptable carrier.

In accordance with a further aspect of the present invention, a method for the interim treatment of vaginal infection is provided comprising, prior to determining the origin of the infection, administering an effective amount of a composition comprising acetic acid and boric acid and a pharmaceutically acceptable carrier to a patient in need thereof.

In accordance with another embodiment of the present invention, the composition may be used for the broad based treatment of skin conditions, particularly skin conditions associated with bacterial, fungal, insecticidal, parasitic and actinomycotic infection and keratinization disorders comprising topically applying to affected areas of the skin an effective amount of a composition comprising acetic acid and boric acid and a pharmaceutically acceptable carrier.

In accordance with a further embodiment of the present invention, the use of a composition comprising acetic acid and boric acid in the preparation of a keratolytic agent in the treatment of parasites such as mites and the likes, is provided.

In accordance with a further embodiment of the present invention, the use of a composition comprising acetic acid and boric acid in the preparation of an insecticidal agent is provided.

According to a further embodiment of the present invention the use of a composition comprising acetic acid and boric acid for the prevention of vaginal infections and skin conditions of bacterial, fungal, parasitic, insecticidal and actinomycotic origin is provided.

DESCRIPTION OF THE INVENTION

The composition of the present invention comprises boric acid and acetic acid in particular amounts, and has been found to be particularly effective in the broad based treatment and prevention of vaginal infections and various skin conditions (including hairy regions of the skin, such as, the scalp, body and pubic regions) related to bacterial, fungal, parasitic, insecticidal and actinomycotic infection and in the treatment and prevention of keratinization disorders.

Advantageously, the compositions may be safely used without the need to determine the nature of the infection by precise medical examination, for example, as an interim form of treatment during or prior to medical diagnosis. This aspect of the invention is particularly useful in the treatment of vaginal infections the symptoms of which may be similar for bacterial and fungal infections and the origin of which may only be determinable by precise medical examination. Examples of symptoms which may be present in either fungal or bacterial vaginal infections include symptomatic vaginal discharge, vaginitis and vaginosis.

The composition of the present invention is used to treat and prevent skin conditions of bacterial, fungal, parasitic, insecticidal and actinomycotic origin and is also effective for treating and preventing keratinization disorders. Examples of bacterial infections include infections caused by Pseudomonas, Staphylococcus and Streptococcus. Examples of fungal infections include dermatocandidiasis caused by *candidiasis albicans* and fungal infections from the genera Trichophyton, Epidermophyton and Microsporum, such as *Tinea pedis* (athletes foot), *Tinea cruris* (jock itch), and *Tinea capitis*. An example of an actinomycotic infection is an infection caused by Streptotrichosis. Other conditions which can be treated using the composition of the present invention include infections from fleas, mites, such as *Sarcoptes scabieii*, Cheyletiella and Acariasis, pediculosis (lice), keratinization disorders, which may be caused by various dermatophytes, such as *Microsporum canis* and felis and conditions caused by various types of non-dermatophytes and ectoparasites.

The composition of the present invention is also useful in controlling dandruff, scaling, seborrhea sicca and oleosa. Psoriasis may also be effectively treated since it has been found that the composition of the present invention is effective in treating the organism Malassezia, which has been linked to Psoriasis.

It has been found that the composition of the present invention acts as a keratolytic agent. This is unexpected and makes the composition particularly useful for treating mites which are located under the skin of a mammal and which would ordinarily be difficult to treat effectively. In this regard, the composition acts by peeling off the skin covering the mite so as to expose the mite directly to the action of the composition.

For treatment and prevention of vaginal infection the composition is most preferably administered in the form of a suppository although other dosage forms are also advantageously envisioned. Advantages to administering the composition as a suppository include convenience, ease of application, increased safety and neatness. Other dosage forms include solutions and douches for douching and the like, shampoos, creams, ointments, gels, creme rinses and foams.

Administering the composition as a cream having a low surface tension is advantageous as it provides a uniform wetting action that assists in composition penetration into vaginal crypts and crevices. It has been surprisingly found that acetic acid assists with penetration.

Providing the composition in the form of a solution, which may initially be provided in a concentrated liquid form, or as a dissolvable powder, tablet or the like requiring the addition of water, saline or other suitable diluent, prior to use, enables the composition to be administered as a vaginal douche. As a vaginal douche, the composition can also be used in a prophylactic manner and for hygienic purposes.

For the treatment of skin conditions the composition is preferably in a form most suitable for topical application and includes creams, ointments, gels, shampoos, creme rinses, foams and solutions, including cleansing solutions.

As mentioned above, acetic acid has antimicrobial capacities and is effective at various percentages against Pseudomonas, Staphylococcus, Streptococcus and various yeasts. Boric acid is an effective antibacterial and antifungal agent.

The amount of acetic acid and boric acid in the composition is an amount which is safe and effective and varies depending on the nature of the composition, the organ and animal being treated and the severity of the infection. Such an amount is determinable by a person of skill in the art. Acetic acid preferably comprises about 0.1% to 10.0% by weight of the composition, more preferably 2.0–5.0% by weight of the composition. Boric acid preferably comprises about 0.1% to 30.0% by weight of the composition, more preferably about 2.0–12.0% by weight of the composition.

Where the composition is applied as a suppository, the active ingredients are combined with inert suppository bases, depending on the nature of the suppository, such as cocoa butter, glycerinated gelatin, hydrogenated vegetables oils, mixtures of polyethylene glycols of various molecular weights and fatty acid esters of polyethylene glycol. Means of creating these suppository bases are known to those skilled in the art. The use of soluble or dispersible bases such as polyethylene glycols or glycol surfactant combinations has the substantial advantage of lack of dependence on melting point approximating body temperature. Moreover, handling, storage and shipping are considerably simplified.

The preparation of such suppository compositions includes well known techniques of rolling (hand shaping), molding (fusion) and cold compression. Suppositories are usually globular or oviform and weigh about 5 gram. Reference is made to *Remington's Pharmaceutical Sciences,* 18th Edition, Chapter 87, pages 1609–13 (1990), the disclosure of which is expressly incorporated herein by reference.

The composition may include a water soluble base. A water soluble base lowers the surface tension of the composition aiding in a more thorough distribution of the composition. A water soluble base also decreases the risk of secondary infection. Illustrative water soluble bases are corn starch, aloe, cocoa butter and the like.

The compositions of the invention may include propylene glycol. Propylene glycol acts as a surfactant and assists in penetration, contact, and absorption of the active ingredients. Propylene glycol also serves as a preservative and as a microbial agent.

The compositions of the invention may also include a non-ionic surfactant, such as polysorbate. Such a surfactant provides better surface contact of the composition with the vaginal mucosa by further reducing surface tension.

The compositions of the invention may also be used as a carrier material for and/or in combination with other medicines, such as antibiotics, spermicidal and parasiticidal agents, anti-inflammatories, thereby further broadening the compositions medical efficacy. It is envisioned that the composition may be combined with for example antibiotics so as to extend the scope of treatment to other types of vaginal infections currently not treatable by the combination of acetic and boric acid alone.

Although, the composition is active, independent of pH, in the presence of blood, pus or vaginal secretions, one particular advantage in combining acetic acid with boric acid is that the pH of the composition may be readily adjusted to allow therapeutic amounts of each component while maintaining the pH at a level that is most effective for the treatment of organs such as the vagina and skin.

The composition of the present invention may also be pH balanced by the addition of a base, such as triethanolamine or sodium hydroxide, to adjust the pH to a level compatible with the organ being treated. In the normal vagina, the pH is between approximately 3.8–4.4. In normal skin the pH is between approximately 5.6–6.6. In order to prevent irritation of the skin or vagina from a composition that is too acidic, the pH is adjusted to a point where the irritation is minimal or nonexistent, while still being effective against microorganisms, including yeast. On the other hand, acetic acid acts to acidify the composition making it possible to more effectively adjust the pH of the composition such that the vaginal areas can be safely and effectively treated. Acetic acid may also assist in removing debris and the likes from the site of action allowing more direct contact for more effective treatment.

A humectant may also be included in the composition of the present invention, such as glycerin, to soothe the area being treated, for example, in cleansing solution compositions.

The composition of the present invention may also include a topical anesthetic such as lidocaine hydrochloride and topical steroids, such as corticosteroid, to provide relief from pain or itching during treatment.

As will be understood by those skilled in the art, the regimen for treating vaginal infection and/or skin conditions will depend on the severity of the infection and the form of the composition. By way of example, where the composition is in the form of a cream, the cream is topically applied to the affected area. Where the composition is in the form of a suppository, the suppository is inserted into the vagina, most preferably once or twice daily for 7 days.

Terms used herein are to be given their usual meaning in the art unless otherwise stated. The term "vaginal infection" means any vaginal infection of, for example, bacterial, fungal or parasitic origin. Examples of some of the microorganisms which cause such infections include microorganisms of the genus Candida, particularly *C. albicans* and *C. tropicalis* and *T. glabrata, Gardneralla vaginalis,* various mixed anaerobic bacteria and Peptostreptococcus bacteria.

The term "skin condition" means any skin condition which results from bacterial, parasitic, fungal, insecticidal and actinomycotic infection and includes keratinization disorders. Examples of microorganisms which can cause such infections include *Candidiasis albicans*, microorganisms of the genera Trichophyton, Epidermophyton and Microsporum, parasites such as *Sarcoptes scabieii,* Streptotrichosis, various dermatophytes, various types of ectoparasites and insects and the likes, for example, fleas, lice and mites.

The term "effective amount" is an amount which is effective in treating a particular infection and is determinable by a person of skill in the art.

Preparation of each of the formulations described herein would be within the ambit of the person of skill in the art, although reference is made to *Remington's Pharmaceutical Sciences,* 18th Edition (1990), the disclosure of which is expressly incorporated herein by reference.

The present invention will now be described by way of reference to the following examples which are not to be construed in such a manner as to limit the scope of the present invention.

EXAMPLE 1

Vaginal Suppository

A suitable formulation for a composition in the form of a suppository for treating vaginal infection is given as follows:

600 mg boric acid (powder)
0.1–10% by weight (glacial) acetic acid
cocoa butter

Preparation

The suppository essentially comprising the above formulation can be prepared as mentioned above in accordance with well known techniques in the art. The amount of cocoa butter may vary but will be sufficient to compound the suppository.

Application

Treatment of the vaginal infection may very depending on the severity of the infection. In general, a suitable treatment regime would be to insert the suppository into the vagina, twice daily for 7 days.

EXAMPLE 2

Vaginal Solution

A suitable formulation for a solution according to the present invention for the treatment of vaginal infection is given as follows, wherein the percentages are given as %w/w of the total composition:

0.1–0.5% boric acid

2% (glacial) acetic acid water

For a douche solution other ingredients may be added and include those typically found in vaginal douches such as other antimicrobial agents, anaesthetics or antipruitics (such as phenol or menthol), astringents and surface active agents. The solution may be initially formed as a concentrated liquid, dissolvable powder or tablet. When use is desired, water may be added, preferably warm in temperature, to produce a solution of desired concentration.

Other ingredients such as propylene glycol, glycerin USP and Polysorbate 20 (Liposorb L20) may be added.

EXAMPLE 3

Skin Treatment and Cleansing Solution

A suitable formulation for a composition in the form of a solution for treatment of skin infection and cleansing is given as follows, in which the percentages are given as %w/w of the total composition:

81% water

2% boric acid powder

2% glacial acetic acid

5% propylene glycol

5% glycerin USP

5% Polysorbate 20 (Liposorb L20)

Preparation

The solution is prepared by adding water to a suitable tank. The remaining ingredients are mixed in slowly until completely dissolved. The mixed solution is uniform and clear. The solution may be further diluted by the addition of water.

Application

The solution can be applied to the infected area of the skin by any suitable means such as cotton wool, cotton swab or the like.

EXAMPLE 4

Shampoo

A suitable formulation for a composition in the form of a shampoo according to the present invention is given as follows, in which the percentages are given as %w/w of the total composition:

| | |
|---|---|
| Water | 59.3–66.1% |
| Methocel F4m | 0.2–0.3% |
| Glucamate DOE 120 | 1.0–1.5% |
| Alpha Olefin Sulfonate (40%) | 20–23% |
| Lauramide DEA | 0.8–1% |
| Boric Acid (powder) | 2% |
| Acetic Acid (glacial-99%) | 2% |
| Cocamidopropyl Betaine | 6–8% |
| Coconut (fragrance) | 0.27% |
| Glycerin USP | 0.5% |
| Safflower Oil | 0.003% |
| Kathon CG | 0.1% |
| Sodium Lactate | 1–2% |

Preparation

Add to a suitable mixing tank, water as above. Add the Methocel F4M and Glucamate DOE 120 slowly. Mix until uniform and completely free of lumps. Continue to add and mix in the remaining ingredients until uniform.

Application

The shampoo can be used by massaging a suitable amount, such as about 5 mls, of the shampoo into the hair and/or body and rinsing off with warm water. The shampoo is suitable for use on all hairy regions of the body including scalp and pubic areas, as often as deemed necessary.

EXAMPLE 5

The susceptibility of selected pathogens to individual and mixtures of acetic and boric acid was investigated, in vitro.

Protocol

Fresh isolates of *Staphylococcus intermedius, Pseudomonas aeruginosa, Candida albicans, Microsporum canis* and *Malassezia pachydermatis* were obtained from VHUP Clinical Veterinary Microbiology Laboratory.

Staphylococcus and Pseudomonas were grown on Mueller-Hinton (M-H) broth overnight at approximately 37° C. and fungi were inoculated into Sabourauds Antibiotic broth medium and incubated at 25° C. for 4 days.

Stock dilutions (2x) of both boric acid and acetic acid were prepared in M-H broth (for bacteria studies) or in Sabourauds Antibiotic Broth (for fungal studies). These concentrations were 1.0%, 4.0%, 7.5% and 10.0%. The stock solutions were used to prepare the full spectrum of all possible combinations of acetic and boric acids in 96 well microtiter plates. All wells were raised to a final volume of 100 ul as required.

The organisms were diluted to an approximate concentration of $10^5$ cfu and 10 ul of this preparation was inolculated into each well with an 8 channel micropipeter.

The microtiter plates containing the bacteria were incubated at 35.5° C. for 18 to 24 hours. The plates containing the fungi were incubated at 25° C. for 3–5 days. The presence of the growth in the wells was recorded. These values determine the Minimum Inhibitory Concentration (MIC) of the acids at individual and mixed concentrations.

The establishment of Minimum Bacterial Concentration (MBC)was carried out as follows:

1 ul was transferred via a 6x6 replicator to a square plate containing the appropriate growth medium for the organism. For the bacterial investigation, the plates were inoculated with bacterial preparation and incubated for 48 hours at 37° C. and visually inspected daily for growth. The results were recorded. For fungal investigation the same aliquots were transferred from wells every 48 hours for 6 days. (A difference of one or less dilution between the MIC and MBC readings indicates a bactericidal interaction. A difference of two or more dilution is interpreted as a bacteriostatic interaction.)

RESULTS

Although Boric acid alone inhibited Staphylococcus, Pseudomonas and Candida, the results surprisingly indicated that a combination of the acids, acetic acid and boric acid, was required to achieve a killing effect on Staphylococcus, Pseudomonas and Candida. It was also found that the bacteria was considerably more sensitive to boric acid concentrations than Candida.

No results were obtained for *Microsporum canis* and *Malassezia pachydermatis* due to no growth in the controls.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for treating an infection of the vagina comprising administering to a patient in need thereof a combination of boric acid and acetic acid and a pharmaceutically acceptable carrier, wherein the composition comprises from 0.1% to 10.0% by weight of acetic acid and from 0.1% to 30.0% by weight of boric acid.

2. A method according to claim 1 wherein the composition is administered in a form selected from the group consisting of a vaginal suppository, cream, ointment, gel, douche, solution, shampoo, creme rinse and foam.

3. A method according to claim 1 wherein the composition further comprises a surfactant.

4. A method according to claim 3 wherein the surfactant is propylene glycol.

5. A method according to claim 1 wherein the composition further comprises a non-ionic surfactant.

6. A method according to claim 5 wherein the non-ionic surfactant is polysorbate.

7. A method according to claim 1 wherein the composition comprises a pH adjuster which adjusts the pH to about that of a vagina.

8. A method according to claim 7 wherein the pH adjuster is triethanolamine.

9. A method according to claim 1 wherein the infection is one caused by a microorganism of the genus Candida.

10. A method according to claim 1 which comprises an interim treatment prior to determining the cause of the vaginal infection.

11. A method for preventing vaginal infection which comprises administering to a patient in need there of an effective amount of a composition comprising acetic acid and boric acid, wherein the composition comprises from 0.1% to 10.0% by weight of acetic acid and from 0.1% to 30.0% by weight of boric acid.

12. A method according to claim 2 wherein said composition is in a form suitable for vaginal treatment.

13. A method according to claim 12 wherein the vaginal infection is that caused by a fungus.

14. A method according to claim 12 wherein the infection of the vagina is of both bacterial and fungal origin.

* * * * *